US00PP18913P2

(12) United States Plant Patent
Vanlaeken

(10) Patent No.: US PP18,913 P2
(45) Date of Patent: Jun. 10, 2008

(54) ***CLEMATIS* PLANT NAMED 'TIE DYE'**

(50) Latin Name: ***Clematis* sp.**
Varietal Denomination: Tie Dye

(76) Inventor: James P Vanlaeken, 3242 Daansen Rd., Walworth, NY (US) 14568

( * ) Notice: Subject to any disclaimer, the term of this patent is extended or adjusted under 35 U.S.C. 154(b) by 0 days.

(21) Appl. No.: 11/488,576

(22) Filed: Jul. 19, 2006

(51) Int. Cl.
*A01H 5/00* (2006.01)

(52) U.S. Cl. ..... Plt./228
(58) Field of Classification Search ..... Plt./228
See application file for complete search history.

(56) References Cited

PUBLICATIONS

Spring Valley Greenhouse, Inc. Catalog 5th edition p. 6 "Jackmanii".*

Spring Valley Greenhouse, inc. Catalog 6th edition p. 2 "Tie Dye".*

* cited by examiner

*Primary Examiner*—Annette H Para

(57) ABSTRACT

A new variety of *Clematis* plant named 'Tie Dye'. The variety is characterized by it's unique color combination, having a violet blue tepal with white marbling throughout.

1 Drawing Sheet

Botanical classification: *Clematis* sp.
Cultivar designation: 'Tie Dye'.

BACKGROUND OF THE VARIETY

The present invention relates to a new and distinct variety of hybrid *Clematis* plant known by the cultivar name 'Tie Dye'.

The new variety was a mutation found growing in a controlled planting of *Clematis* Jackmanii at a clematis nursery in Walworth, N.Y. in 2001. Plants were asexually propagated and observed over the next four years. Asexually propagation by vegetative cuttings has shown that the propagules are identified to the original plant and all distinguished characteristics. The stability of the variety is evidenced by the distinguished characteristics remaining true to form from generation to generation. The parentage of the variety is unknown.

SUMMARY OF THE INVENTION

Among the features which distinguish the new variety form other present available and known commercial clematis cultivars are the unique color of the flower. The flower has violet purple tepals with white marbling through out. It's vigorous habit and profuse blooming makes this variety a very desirable plant.

RELEVANT PRIOR ART

The new variety is some what similar in appearance to *Clematis* sp. 'Jackmanii' variety as shown in Spring Valley, Inc. ($5^{th}$ Edition) on page 6. Both flowers are similar in that they both have 4–5 tepals and whitish/pink tipped stamens. Their growth habit, time of bloom, and number of blooms are identical. The difference between the two are the white marbling which occurs on the cultivar Tie Dye. Picture of Tie Dye on Page 2 of Spring Valley catalog $6^{th}$ edition shows it is a unique flowering *Clematis* as compared to other varieties available.

BRIEF DESCRIPTION OF THE PHOTOGRAPH

The accompanying photograph illustrates the overall appearance of the new variety. The flowering and foliage colors as shown are, within the limitations of color photography, accurate and true reproductions of the actual colors of new variety. The photographic view is a front elevation of typical *Clematis* sp. 'Tie Dye'.

BOTANICAL DESCRIPTION

The following information is based on a three year old plant grown in 50% shade in a five gallon container in a covered greenhouse with 60° F. ambient night temperatures and 75° F. ambient day temperatures in Walworth, N.Y. Color references are based on using the PANTONE® matching system.

1. Plant:
   - *A. Form.*—Upright climbing or spreading.
   - *B. Growth.*—Vigorous, vining. 1. Height: Approximately 8 feet to 15 feet. 2. Diameter/Spread: Approximately 2 feet to 3 feet.
   - *C. Foliage.*—Deciduous, compound-trifoliate, opposite. 1. Size, typical and observed: a. Compound leaf length 6 inches, width 5 inches. b. Individual leaflets length 2.5 to 3.5 inches, width 1 to 2 inches. c. Leaflets per compound leaf: 3.
2. Quantity of leaves per stem: Typically and observed: about 48.
3. Color:
   - *a. Upper surface.*—Dark green (PANTONE® #575U).
   - *b. Lower surface.*—Medium green (PANTONE® #576U).
4. Shape:
   - *a. Leaflets.*—Base is rounded, margin is untoothed with glabrous edge, apex is pointed.
5. Texture:
   - *a. Upperside.*—Smooth and veined.
   - *b. Underside.*—Ribbed and glabrous.

*c. Veination pattern.*—Leaflets palmatic with green coloration on upper and lower.

6. Petiole:

*a. Color.*—Light green (PANTONE® #582U).

*b. Length, typical and observed.*—1 to 3 inches.

*c. Diameter, typical and observed.*—⅛ inch.

*d. Glabrous.*—Yes.

D. Wood:

*1. New shoots.*—a. Color: Medium green (PANTONE® #575C). b. Bark: Smooth. c. Internodes: Cylindrical, approximately 5 to 6 inches in length and ⅛ inch in diameter.

*2. Old wood.*—a. Color: Medium brown (PANTONE® #464C). b. Bark: Smooth ⅛ inch in diameter. c. Internodes: Cylindrical, approximately 5 to 6 inches in length and ⅛ inch in diameter and glabrous.

E. Hardiness: US Zones 4 through 8.

*1. Low temperature tolerance, typical and observed.*—−10° F. to 0° F.

*2. High temperature tolerance, typical and observed.*—90° F. to 110° F.; requires 6 to 8 weeks dormancy at 35° F. to 40° F. to remain vigorous.

F. Disease:

*1. Subject to any disease that affects clematis.*—a. Wilt. b. Botrytis. c. Powdery mildew.

G. Pests:

*1. Subject to any pest that normally affect clematis.*—a. Aphids. b. Spider mites. d. Slugs and snails.

II. Flower

A. Blooming habit: June and July based on climate in Rochester, N.Y. area.

B. Bud:

*1. Size.*—Typical and observed from about 1.5 to 2 inches in length and about ½ to 1 inch in diameter.

*2. Form.*—Ovate base with pointed tip.

*3. Color.*—Light green with white veins (PANTONE® #583U).

C. Stem:

*1. Dimension, typical and observed.*—Length 3 to 4 inches, diameter 1/16 inch.

*2. Aspect.*—Vertical.

*3. Strength.*—Erect.

*4. Color.*—Green (PANTONE® #378C).

D. Bloom:

*1. Size.*—Typical and observed from about 3 to 5 inches in diameter with a depth of about ¾ inch.

*2. Form.*—Cross shaped with 4 to 5 tepals of equal size seldom overlapping.

*3. Color upper surface.*—Violet purple (PANTONE® #266U) with light violet (PANTONE® #530U) marbling.

*4. Color of lower surface.*—Light violet purple (PANTONE® #528U) with prominent raised veining of violet red (PANTONE® #244U).

*5. Characteristics.*—Born on 3 to 4 inch stems on new growth.

*6. Quantity.*—1 bloom per stem from 2 to 3 to several hundred blooms per plant depending on the age and size of plant.

*7. Lastingness.*—3 to 6 days as a cut flower or 7 to 10 days on plant.

E. Tepals:

*1. Form.*—Irregular in shape starting with a wide wedge shaped ½ inch base expanding half way up to 1.5 inches at widest point and then tapering down to a pointed apex. The overall tepal length being 2 to 3 inches with irregular toothed edges.

*2. Arrangement of tepals.*—Regularly arranged seldom overlapping.

*3. Fragrance.*—None.

*4. Color upper surface.*—Violet purple (PANTONE® #266U) with light violet (PANTONE® #530U) marbling.

*5. Color of lower surface.*—Light violet purple (PANTONE® ™528U) with prominent raised veining of violet red (PANTONE® #244U).

III. Reproductive Organs

A. Stamens, filaments and anthers:

*1. Arrangement.*—Regularly arranged.

*2. Stamens.*—Typical and observed 40 to 45 per bloom, length 9/16 inch.

*3. Anthers.*—Length 3/16 inch (PANTONE® #182U) whitish/pink.

*4. Filament.*—White.

B. Pollen:

*1. Color.*—White.

*2. Amount.*—Scarce.

C. Style: Bunched, even, average length (PANTONE® #182U) whitish/pink.

D. Stigmas:

*1. Color.*—White.

E. Seed, typical and observed:

*1. Diameter.*—1/16 inch.

*2. Thickness.*—1.32 inch.

*3. Color.*—(PANTONE® #577U) medium green.

*4. Shape.*—Round.

*5. Quantity per bloom.*—30 to 40.

*6. Description.*—¾ inch long persistent style which is clothed with silky white hairs.

I claim:

1. A new and distinct variety of *Clematis* plant named 'Tie Dye' as shown and described herein.

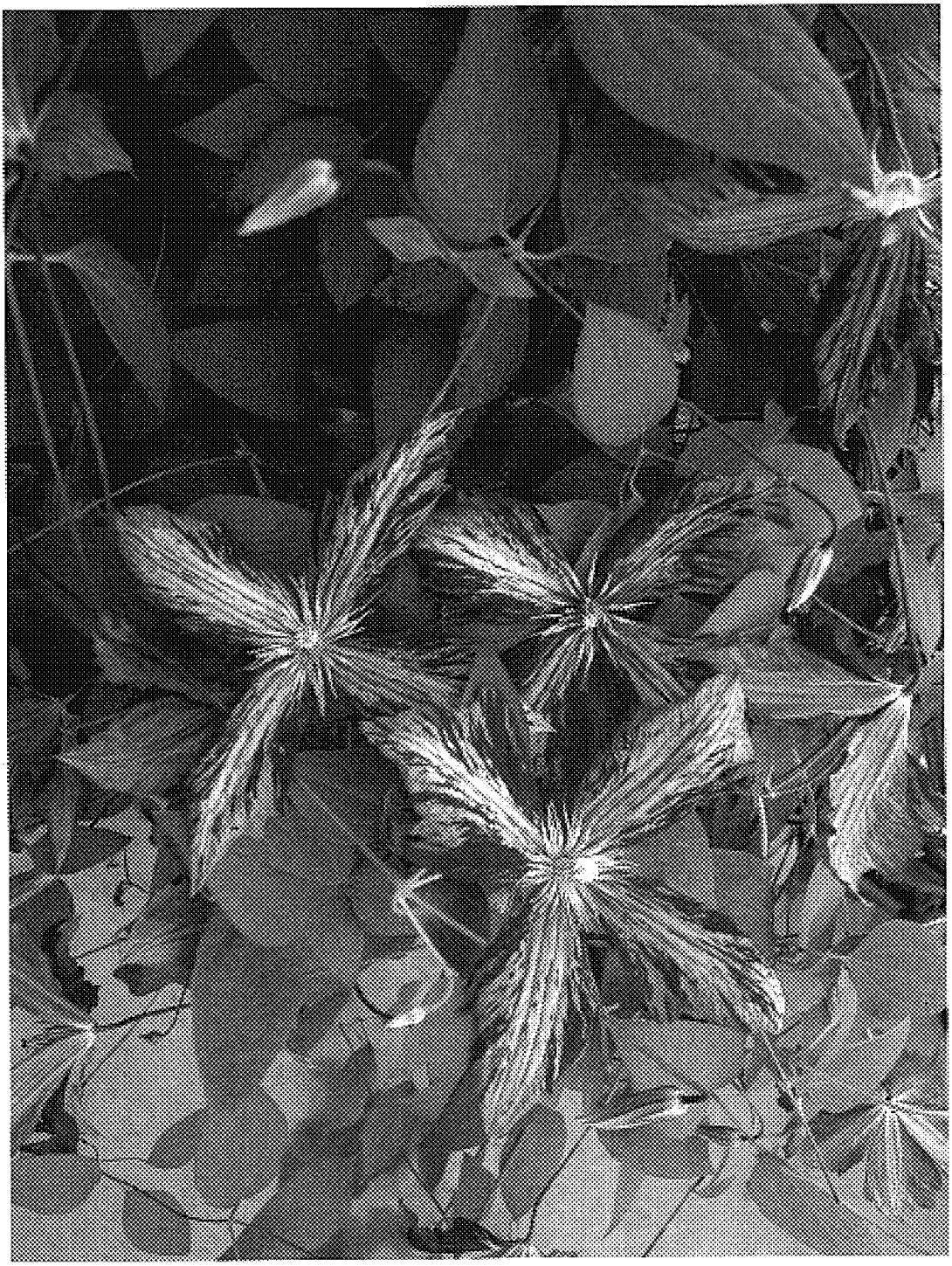

* * * * *